United States Patent [19]

Moore, Jr.

[11] 4,028,345
[45] June 7, 1977

[54] PROCESS FOR THE PREPARATION OF AZODINITRILES FROM AMINONITRILES IN THE PRESENCE OF A SURFACTANT

[75] Inventor: Earl Phillip Moore, Jr., Hockessin, Del.

[73] Assignee: E. I. Du Pont de Nemours and Company, Wilmington, Del.

[22] Filed: Oct. 3, 1975

[21] Appl. No.: 618,761

Related U.S. Application Data

[63] Continuation-in-part of Ser. No. 540,084, Jan. 10, 1975, abandoned.

[52] U.S. Cl. .............................. 260/192; 260/464; 260/465.5 R
[51] Int. Cl.² ....................................... C07C 107/02
[58] Field of Search ................................... 260/192

[56] References Cited
UNITED STATES PATENTS

| | | | |
|---|---|---|---|
| 2,711,405 | 6/1955 | Anderson | 260/192 |
| 2,713,576 | 7/1955 | De Benneville | 260/192 |
| 3,390,146 | 6/1968 | Nield et al. | 260/192 |
| 3,775,395 | 11/1973 | Koyanagi et al. | 260/192 |
| 3,783,148 | 1/1974 | Fuchs | 260/192 |

Primary Examiner—Floyd D. Higel

[57] ABSTRACT

The preparation of aliphatic azodinitriles by a process comprising reacting an alpha-aminonitrile selected from

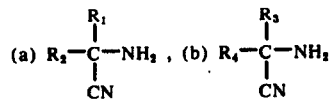

and mixtures thereof wherein $R_1$, $R_2$, $R_3$ and $R_4$ are selected from (1) hydrocarbyl radicals of 1 to 8 carbon atoms, (2) hydrocarbyl radicals of 1 to 8 carbon atoms substituted with carboxyl, hydroxyl or —OR wherein R is selected from a hydrocarbyl radical of 1 to 4 carbon atoms, (3) cyclohydrocarbyl radicals of 3 to 6 carbon atoms and (4) cyclohydrocarbyl radicals of 3 to 11 carbon atoms formed by combining $R_1$ and $R_2$ or $R_3$ and $R_4$ with 5 to 15% by weight based on the reaction mixture of a metal hypochlorite, $M(OCl)_x$ where M is selected from sodium, potassium or calcium and $x$ is the valence of M, in an aqueous medium in the presence of 0.25 to 10% by weight, based on the weight of aminonitrile, of a surface active compound or mixtures thereof having an HLB of 8 to 35 at a temperature of −10° C to 30° C, said hypochlorite and alpha-aminonitrile being present in an equivalent ratio of 1:1 to 2:1 of hypochlorite to aminonitrile and recovering from the reaction mixture an aliphatic azodinitrile of the formula

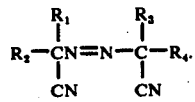

20 Claims, No Drawings

PROCESS FOR THE PREPARATION OF AZODINITRILES FROM AMINONITRILES IN THE PRESENCE OF A SURFACTANT

CROSS REFERENCE TO RELATED APPLICATION

This is a continuation-in-part of copending application Ser. No. 540,084, filed Jan. 10, 1975 now abandoned.

BACKGROUND OF THE INVENTION

1. Field of the Invention

This invention relates to an improved process for the preparation of aliphatic azo compounds. More specifically this invention relates to a process for the preparation of aliphatic azodinitrile compounds by reacting an aqueous hypochlorite solution with an aminonitrile.

2. Prior Art

The symmetrical azobis(alkanonitriles) and their derivatives have been recognized for over 25 years as useful, highly efficient free-radical polymerization initiators but the slow evolution of feasible and/or economical preparative routes have retarded the commercial development of these unique compounds.

The oldest method for producing aliphatic azonitriles commercially, described by Thiele and Heuser in Ann. 290, 1–43 (1896) is based upon the use of relatively expensive hydrazine and its derivatives as a principal raw material. Castle, U.S. Pat. No. 2,515,628, reacted ketones with sodium cyanide and hydrazine hydrochloride in aqueous medium and the resulting hydrazo compounds were oxidized in water or alcohol to the azos. Robertson, U.S. Pat. No. 2,586,995, prepared the ketazines from ketones and hydrazine hydrate, contacted them with liquid hydrogen cyanide to give hydrazo compounds and oxidized these to the azos. Both of the above procedures gave poor-to-fair yields of azonitriles. A significant process improvement in the hydrazine-based route was made by Koyanagi, et al., U.S. Pat. No. 3,775,395, who reacted a ketone, a hydrazine compound and hydrogen cyanide in aqueous medium in the presence of a surface active agent to form the hydrazo compound. Overall yields of azos were excellent.

A second method of producing azonitriles is described by Anderson, U.S. Pat. No. 2,711,405, which involves reacting the cyanohydrin of an aliphatic keton with ammonia to form an aminonitrile and oxidatively coupling the aminonitrile to form the azo using an alkali metal or alkaline earth metal hypochlorite in aqueous medium. De Benneville, U.S. Pat. No. 2,713,576, claimed essentially the same process with the addition of alkyl hypochlorites and restriction of aminonitriles to those of acetone, methyl ethyl ketone and diethyl ketone. Although the process as disclosed in the Anderson and De Benneville patents is useful for the preparation of azobisisobutyronitrile from the aminonitrile of acetone, the coupling step results in extremely poor yields when applied to aminonitriles of higher molecular weight ketones. A process improvement which enables azonitriles to be prepared from aminonitriles of higher molecular weight ketones in good yields is reported by Fuchs, U.S. Pat. No. 3,783,148. Methanol or ethanol is employed as a reaction solvent in proportion to the amounts of aminonitrile and hypochlorite solution used such that, at the completion of the reaction, the alcohol concentration is at least 70% by volume. The alcohol maintains a homogeneous system throughout the reaction and specifically prevents separation of the intermediate, highly hydrophobic chloramines.

The Fuchs process, however, has its drawbacks. For economic reasons, the alcohol solvent must be recovered; even then, some loss of alcohol occurs due to evaporation, side reactions, etc. The alcohol also interacts with the hypochlorite compound, giving an organic alkyl hypochlorite, which can decompose in a highly exothermic reaction which imposes severe restrictions on the temperature and conditions under which the azonitrile preparation can be carried out.

The Fuchs process also has other disadvantages. In order to minimize the decomposition of alkyl hypochlorite and more easily control the heat load, the aminonitrile and hypochlorite are preferably added simultaneously. The molar ratio of hypochlorite to aminonitrile must be maintained in the range of 1.4 to 1.8 during the entire course of the addition. During the addition, the temperature must be held below −5° C. Equipment and manpower requirements to maintain these stringent conditions are costly. Furthermore, use of other reaction conditions, such as the addition of the amino compound to the hypochlorite, which would enhance both yield and purity of the resulting azo compound, are obviated. In addition, product slurries with low solids content are obtained, because of the alcohol and water requirements to effect this process. This incurs considerable liquid handling and disposal per pound of product with unfavorable labor costs and production limits.

It is therefore desirable to discover a process which is free of the above disadvantages.

SUMMARY OF THE INVENTION

The present invention involves a process for preparing aliphatic azodinitriles free of the above disadvantages. Now it has been found that aliphatic azodinitriles can be prepared by reacting a metal hypochlorite with an aminonitrile in water containing a surfactant. Accordingly, the process of the present invention comprises reacting an alpha-aminoitrile of the formula

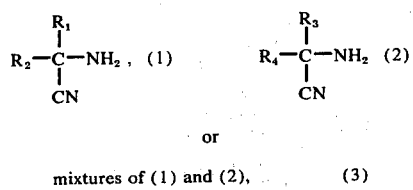

wherein $R_1$, $R_2$, $R_3$ and $R_4$ are selected from the group consisting of (1) aliphatic hydrocarbon radicals of 1 to 8 carbon atoms, optionally substituted with a carboxyl group, an hydroxyl group or an alkoxy group represented by —OR wherein R is an acylic aliphatic hydrocarbon radical of 1 to 4 carbon atoms, (2) cycloaliphatic hydrocarbon radicals of 3 to 6 carbon atoms and (3) cycloaliphatic hydrocarbon radicals of 3 to 11 carbon atoms formed by combining $R_1$ and $R_2$ or $R_3$ and $R_4$, with a metal hypochlorite in an aqueous medium in the presence of a surface active compound and recovering from the reaction mixture an aliphatic azodinitrile compound that may be of the formula

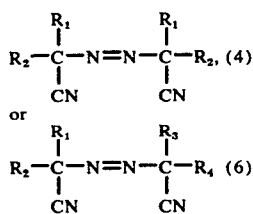
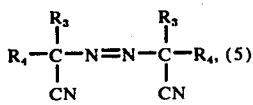

wherein $R_1$, $R_2$, $R_3$ and $R_4$ are as defined above. In the above azodinitrile formula $R_1$ and $R_2$ as well as $R_3$ and $R_4$ include both separate radicals and combined single cyclic radicals. $R_1$ and $R_2$ need not be the same as $R_3$ and $R_4$, that is, the structure of the azonitrile to the left of the —N=N— group need not be the same as the structure to the right. Thus the azodinitrile may be symmetrical or unsymmetrical.

The particular azodinitrile compound that results from the process of the present invention depends on which of the starting aminonitrile compounds are used. For example, when the aminonitrile of formula (1) above is used the resulting compound is represented by formula (4) above and for the aminonitrile of formula (2) the produce is represented by formula (5) while formula (6) represents the product of mixed aminonitriles. When mixed aminonitriles are used the product may also include azo compounds of formula (4) and (5).

Representative examples of $R_1$, $R_2$, $R_3$ and $R_4$ include aliphatic hydrocarbon radicals such as methyl, ethyl, propyl, isobutyl, neopentyl, n-octyl and the like.

Representative substituted aliphatic hydrocarbon radicals include 2-carboxyethyl, 4-hydroxybutyl, 2-methyl-2-methoxypropyl and the like.

Representative cycloaliphatic hydrocarbon radicals include cyclopropyl, cyclohexyl and the like.

Representative cycloaliphatic hydrocarbon radicals formed by combining $R_1$ and $R_2$ or $R_3$ and $R_4$ include

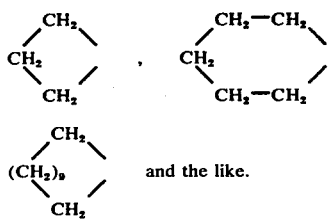

In the process of the present invention, two molecules of an amino compound selected from the group consisting of

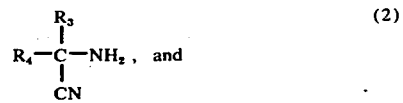

mixtures of (1) and (2)  (3)

wherein $R_1$, $R_2$, $R_3$ and $R_4$ are as defined above are coupled to form the azodinitrile of the present invention. The coupling of the two molecules is accomplished in an aqueous medium with a metal hypochlorite represented by the formula $M(OCl)_x$, wherein M is selected from sodium, potassium and calcium and $x$ is the valence of the M ion, and a surface active compound selected from the group consisting of an anionic, cationic, nonionic, amphoteric and mixed surface active agents or surfactants.

The reaction stoichiometry of the process of this invention where the amino compound is represented by the formula (1) above can be represented by the following equation:

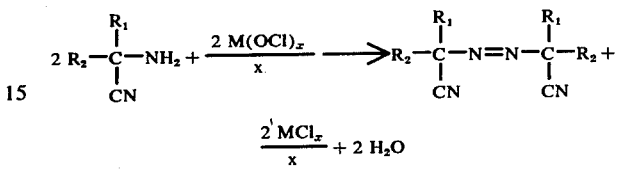

$$\frac{2\,MCl_x}{x} + 2\,H_2O$$

wherein $R_1$, $R_2$, M and $x$ are as defined above. Where the amino compound is represented by the formula (2) above or (1) and (2) a similar equation can be written.

It will be understood that the starting aminonitrile compound of formulas (1) and (2) may be the same but the above formulas were used to illustrate that they may be different.

This reaction is believed to proceed through an intermediate step in which a chloramine is formed.

In the process of the invention, the equivalent ratio of hypochlorite to aminonitrile is not critical. However, at equivalent ratios below 1:1 of hypochlorite to aminonitrile the yield is less desirable. At equivalent ratios above 2:1 there is no advantage. Generally, the equivalent ratio of 1:1 to 2:1 will give high yields although the ratio of 1.2:1 to 1.8:1 is preferred because of the especially high yields that result. The equivalent ratio referred to herein is defined as the equivalent of metal hypochlorite per mole of aminonitrile. An equivalent of metal hypochlorite is a mole of the hypochlorite divided by the valence of the metal. An equivalent of aminonitrile is the same as the molar amount of aminonitrile.

The amino compounds used as starting materials in the process of the present invention may be selected from the formulas given above numbered (1), (2) and combinations of (1) and (2) as defined above. The amino compounds of the present invention can be obtained from commercial sources or may be prepared by methods well known in the art, for example, by the method described by Anderson in U.S. Pat. No. 2,711,405. A procedure that can be used to obtain the amino compounds involves charging a ketone of the structure described to a platinum-lined pressure vessel and cooling this to dry ice-acetone temperature and then adding 5–10 grams of ammonia. Hydrogen cyanide is then introduced in portions in an amount equimolar to that of the ketone. The reaction vessel is warmed to room temperature and pressurized to 50 psig with ammonia, heated to 40° C. and held at 40° C. and 50 psig for 8 hours and finally cooled and the product is discharged from the vessel.

The hydrochlorite of the present invention is a metal hydrochlorite represented by the formula $M(OCl)_x$ where M is selected from sodium, potassium and calcium and $x$ is the valence of M. For reasons of convenience ane economy, sodium hypochlorite is the preferred hypochlorite. Sodium hypochlorite can be prepared by passing chlorine gas in an aqueous sodium hydroxide solution at about 0° C. or it can be produced commercially. Other hypochlorites can be prepared analogously.

The surface acive compounds of the present invention are defined as any compound or mixture of compounds that affects the surface tension when mixed with water and is not adversely affected in its properties if it reacts with the hypochlorite, aminonitrile, chloramine intermediate or final product of the present invention.

The use of the surface active agents of the present invention is a critical feature of this invention. The inclusion of a surfactant in the process of coupling an aminonitrile to give an azonitrile with hypochlorite enables the reaction quite surprisingly to proceed in strictly aqueous medium. While the function of the surfactant in promoting this coupling reaction is unknown, it may be as a "catalyst" for the reaction of base (e.g., NaOH) with intermediate formed chloramines and/or it may serve as a "solubilizer" for the chloramine and base, or it may perform some other function which enables a reaction to occur.

Surfactants for preparing emulsions are discussed by Paul Becher in "Emulsions, Theory and Practice", ACS Monograph No. 162, 1965. On pages 232–255, Becher discusses the importance of the Hydrophilic-Lipophilic Balance of a surfactant (HLB for short) on its ability to serve as an emulsifying agent in a particular application. The HLB numbers which have been assigned to many surfactants indicate balance in their affinity for water (hydrophilic) or non-polar organic liquids (lipophilic). A high HLB number indicates high water solubility and low organic solubility, a low number indicates a high organic solubility and low water solubility.

In the process of this invention, the apparent importance of HLB numbers of surfactants on their ability to cause the reaction of sodium hypochlorite and aminonitrile was found. Surfactants or mixtures thereof with HLB numbers within the range of about 12.0 to about 35.0 will enable 2,2'-azobis(2,4-dimethylpentanenitrile) to be produced from 2-amino-2,4-dimethylpentanenitrile. To prepare 2,2'-azobis(2,4-dimethyl-4-methoxypentanenitrile) from 2-amino-2,4-dimethyl-4-methoxypentanonitrile, surfactants or mixtures thereof in the HLB range of about 8.0 to about 30.0 are needed. Other azonitriles can generally be produced with surfactants or mixtures thereof within the range of about 8.0 to about 35.0 HLB range.

The surfactants or surface active agents useful in the process of the present invention may be a mixture of said surfactants or surface active agents. Thus, in surfactant mixtures, one component of the mixture may have a HLB number outside the range described herein as long as the HLB of the mixture is within said range.

The surface active compounds of the present invention are referred to as surface active agents or surfactants. Substantially all of the surfactants of the present invention are included in the categories of nonionic, cationic, anionic, amphoteric and mixtures involving combinations of two or more nonionic, cationic, anionic and amphoteric surfactants.

The most important of the surfactants of the present invention are included in the categories of nonionic, cationic and mixtures involving combinations of two or more nonionic and cationic surfactants.

Although the presence of a surface active compound in the process of the present invention is critical, the amount may vary widely. As little as 0.25% by weight of surface active compound based on the aminonitrile can be used and while the upper limit is not critical, there is no advantage in using more than 10% by weight. For example, at levels above 10% by weight there is no improvement in yield. The preferred range however of 1.0 to 4% by weight or surface active based on the aminonitrile gives the most desirable yield.

The ease and convenience with which the inventive process for preparing azonitriles can be carried out to give superior yields of products will be evident when the process is described.

The atmospheric pressure system is entirely aqueous, requiring no organic solvent to be present as a promoter or co-solvent with water. The surfactant is mixed with the water as is the sodium hypochlorite or other metal hypochlorite in the preferred system and the aminonitrile is added with sufficient cooling to handling the heat load. Cooling requirements are less demanding than in the Fuchs process because there is not loss of active halogen through methyl hypochlorite decomposition.

During the reaction period, it is observed that an emulsion of milk-like appearance forms, due apparently to the emulsification of water immiscible intermediate chloramine compounds formed from the aminonitrile and sodium hypochlorite, except in the case where $R_1$, $R_2$, $R_3$ and $R_4$ are methyl, and the intermediate chloramine is water soluble. Further reaction of the emulsified chloramines and sodium hydroxide in the system to give the azonitrile takes place most likely in the confines of the emulsion droplets, giving a product mixture which is partially or almost entirely an emulsion. Because of this, it is necessary to add an agent to effect precipitation. Sodium bisulfite serves this purpose admirably and additionally acts to destroy residual sodium hypochlorite, chloramines and other oxidizing impurities and thereby give a cleaner product. Acid such as hydrochloric or sulfuric is introduced during the product workup to enhance the activity of sodium bisulfite by converting it in part or whole to sulfur dioxide, a powerful reducing agent. Obviously other inorganic salts may be added to effect the breaking of the emulsion and sulfur dioxide gas may be used to destroy oxidizing impurities. Other techniques for breaking emulsions well known in the chemical art can, of course, be employed, as can other reducing agents be used. In the case where $R_1$, $R_2$, $R_3$ and $R_4$ are methyl, the product formed appears to be an emulsion of milk-like appearance but the product is entirely a solids suspension and therefore an emulsion breaking or precipitating agent is not required. Thus, for example, sodium bisulfite or $SO_2$ and hydrochloric or sulfuric acids are not required for the preparation of 2,2'-azobis(isobutyronitrile). However, the use of a precipitating agent results in a better quality 2,2'-azobis-(isobutyronitrile).

The use of the above precipitating agents and acids can also be conveniently used for preparing 2,2'-azobis(isobutyronitrile).

The manner in which the sodium hypochlorite and aminonitrile are combined is a matter of choice. The reactants can be added in separate streams to a body of water containing the surfactant or the aminonitrile can be added to a sodium hypochlorite solution containing the surfactant. This latter method which is preferred is not possible with the Fuchs methanol system where simultaneous addition of reactants into a large volume of methanol is required to keep the reactants in solution. Furthermore, the Fuchs process requires that a large volume of water be added to precipitate the azo compounds. In our preferred system much higher azo solids slurries are possible than with the Fuchs process, enabling higher throughput with time and labor savings providing marked economic benefits. Thus, while product slurries with about 3% solids are obtained with Fuchs process, the solids content of slurries of the present invention is limited only by the upper practical limit of the hypochlorite concentration, which for the preferred sodium hypochlorite is about 15–16%. At this upper limit of sodium hypochlorite concentration, a slurry solids content of greater than 15% can be obtained. Actually, however, any concentration of sodium hypochlorite less than about 16% can be used, but 5–15% is preferred. With less than 5%, yields of product tend to drop off. However, calcium hypochlorite, which is available as a 100% active material, is diluted to attain the preferred 5–15% range. Potassium hypochlorite solutions of the above concentration can also be preferred.

Among the surfactants useful in the present process, those classed as cationic are preferred since they are more efficient than the nonionic, anionic and amphoteric types. For example, a 1% concentration of a cationic surfactant, based upon aminonitrile weight, is roughly equal in performance to 4% nonionic surfactant. Cationic surfactants also tend to give highest yields of azonitrile products. Mixtures of surfactants of the same and different type are useful and can be employed if desired.

Representative examples of nonionic surfactants include complex polyoxyalkylene glycols, polyoxyalkylene fatty acids esters, polyoxyalkylene alkyl aryl ethers, polyoxyalkylene fatty alcohol ethers, polyoxyethylene sorbitol fatty acid esters, alkanol-amides, alkanolimides, amine oxides, polyoxyethylene sorbitan fatty acid esters, alkylene oxide-ethylene diamine condensation compounds, tertiary amines-alkylene oxide condensation products of primary fatty amines and others disclosed in McCutcheons' "Detergents & Emulsifiers", North Americal Edition, 1974 Annual, published by McCutcheon's Division, Allured Publishing Corporation, Ridgewood, N.J.

Representative examples of the above indicated nonionic surfactants are shown in the tables that follow with their trade names and manufacturers:

TABLE I

| Complex Polyoxyalkylene Glycols | |
|---|---|
| Pluronic L-64 (BASF Wyandotte Co.) | Condensate of ethylene oxide with a hydrophobic base formed by condensing propylene oxide with propylene glycol |
| Pluronic 17R8 (BASF Wyandotte Co.) | Condensate of propylene oxide with a hydrophilic base formed by condensing ethylene oxide with ethylene glycol |

TABLE II

| Polyoxyalkylene Fatty Acid Esters | |
|---|---|
| Emcol H-35A (Witco Chemical Corp.) | Polyethylene glycol (400) monostearate |
| Hodag 60-L (Hodag Chemical Corp.) | Polyoxyethylene glycol (600) monolaurate |
| Lipal 15T (PVO International) | Polyoxyethylene tallate |

TABLE III

| Polyoxyalkylene Alkylaryl Ethers | |
|---|---|
| Igepal CO-630 (GAF Corp.) | Nonylphenoxypoly(ethyleneoxy) ethanol |
| T-DET DD-9 (Thompson-Hayward Chem. Co.) | Dodecylphenol-ethylene oxide adduct |
| Poly-Tergent B-350 (Olin Corp.) | Nonylphenoxy polyethoxyethanol |

TABLE IV

| Polyoxyalkylene Fatty Alcohol Ethers | |
|---|---|
| Ameroxol OE-20 (Amerchol Corp.) | Ethoxylated oleyl alcohol |
| Arosurf 66-E20 (Ashland Chem. Co.) | Polyoxyalkylated isostearyl alcohol |
| Brij 35 (ICI America, Inc.) | Polyoxyethylene (23) lauryl ether |
| Merpol HCS (Du Pont Co.) | Polyoxyethylene lauryl ether |

TABLE V

| Polyoxyethylene Sorbitol Fatty Acid Esters | |
|---|---|
| Atlas G-1471 (ICI America, Inc.) | Polyoxyethylene sorbitol lanolin deriv. |
| Atlas G-1086 (ICI America, Inc.) | Polyoxyethylene sorbitol oleate |

TABLE VI

| Alkanolamides and Alkanolimides | |
|---|---|
| Aminimide 56203 (Ashland Chem. Co.) | Dimethyl(2-hydroxypropyl)amine laurimide |
| Alkamide 2104 (Alkaril Chem. Co.) | Coconut diethanolamide |
| Clindrol Superamide 100L (Clintwood Chem. Co.) | Lauric diethanolamide |

TABLE VII

| | Amine Oxides |
|---|---|
| Ammonyx CO | Cetyl dimethyl amine oxide |
| SO | Stearyl dimethyl amine oxide |
| LO | Lauryl dimethyl amine oxide |
| (Onyx Chem. Co.) | |

TABLE VIII

| Polyoxyethylene Sorbitan Fatty Acid Esters | |
|---|---|
| Drewmulse POE-SMO (PVO International) | Ethoxylated sorbitan monooleate |
| Hallco-CPH-375-N (C. P. Hall Co.) | Polyoxyethylene (20) sorbitan monolaurate |
| Tween 60 (ICI America, Inc.) | Polyoxyethylene (20) sorbitan monostearate |

TABLE IX

| Alkylene Oxide-Ethylene Diamine Condensation Compounds* | |
|---|---|
| Tetronic 504, 704, 904, etc. (BASF Wyandotte Corp.) | Compounds formed by addition of propylene oxide to ethylene diamine, followed by the addition of ethylene oxide |

*Also considered as cationic surfactants in acid medium.

TABLE X

| Tertiary Amines-Alkylene Oxide Condensation Products of Primary Fatty Amines* | | |
|---|---|---|
| Varonic | K215 | Ethoxylated coco amine |
| | K202P | Propoxylated fatty amine |
| | T215 | Ethoxylated tallow amine |

*Also considered as cationic surfactants in acid medium.

Nonionic surfactants in addition to those falling in the above classes or compounds that are within the scope of the present invention include lecithin and its derivatives such as soya lecithin, silicone glycol copolymers, fluorochemical compounds, complex polyesters of polyoxyethylene glycol phosphate esters, polymers such as poly(vinyl alcohol) resins, glycol esters such as diethylene glycol oleate, propylene glycol monolaurate and sorbitan monopalmitate.

Cationic surfactants include various types of nitrogen containing compounds such as fatty alkyl amines and their salts and quaternary ammonium compounds or more specifically tetraalkyl ammonium compounds. Tetraalkyl ammonium halides are considered to be the most important type of cationic surfactants. The tetraalkyl ammonium chlorides or bromides are preferred. The tetraalkyl ammonium chlorides are considered the most preferred cationic surfactant. What is meant by tetraalkyl ammonium in the compounds described herein is that they contain a nitrogen atom to which four separate carbon atoms are attached.

Representative examples of tetraalkyl ammonium surfactants of the present invention include:

| Compound | Trade Name | Manufacturer |
|---|---|---|
| Disoya dimethyl ammonium chloride | Arquad 25–75 | Armak Co. |
| Ditallow imidazolinium quaternary salt | Alkaquat T | Alkaril Chemicals |
| Cetyl trimethyl ammonium bromide | Retarder LAN | Du Pont Co. |
| Quaternized polyoxyethylene cocoamine | Ethoquad C/25 | Armak Co. |
| Tallow Trimethyl ammonium chloride | Arquad T-50 | Armak Co. |
| Tetradecyl trimethyl ammonium chloride | | Armak Co. |
| Dodecyl trimethyl ammonium chloride | Arquad 12–50 | Armak Co. |
| Hexadecyl trimethyl ammonium chloride | Arquad 16–50 | Armak Co. |
| Octadecyl trimethyl ammonium chloride | Arquad 18–50 | Armak Co. |

For economic reasons the alkyl ammonium chloride compounds are preferred.

Representative examples of anionic surfactants include the salts of complex organic phosphate esters which include GAFAC LO-529 (GAF Corporation), a sodium salt of a complex organic phosphate ester; DEXTROL EMULSIFIER SW-90 (Dexter Chemical Co.), a potassium salt of a complex organic phosphate ester; and ZELEC UN (Du Pont Co.) a complex organic phosphate ester (unneutralized) which is neutralized with sodium or potassium hydroxide or a trialcoholamine such as triethanolamine or any organic or inorganic base which will give a water soluble or water dispersible phosphate salt and will not react to the extent that its properties will be adversely affected with the other components in the system.

Representative examples of amphoteric surfactants include those with a dual character such as cationic-anionic such as:

| Velvetex BCW (Textilana Corp.) | Coco dimethyl ammonium carboxylic acid betaine; |
|---|---|

The mixed surfactants of this invention are mixtures of two or more of the above surfactants.

The rate at which the aminonitrile can be added to the hypochlorite and surfactant mixture depends on the size of the batch and the capabilities of the cooling equipment. However, the rate can be much more rapid than in prior art processes utilizing methanol. The cooling requirements of the present process is markedly lower than those of the process involving methanol. The methanol process must avoid the highly exothermic decomposition of methyl hypochlorite. Therefore, the process of the present invention can be operated at higher temperatures than those possible in the methanol process and thus permit an economic benefit over the methanol process because of the much lesser need for cooling equipment and associated systems. The preferred temperature of the present process is 5° C. to 15° C. but temperature may vary beyond our preferred temperature range in the process of the present invention. Desirable yields can be obtained at temperatures as low as −10° C. and as high as 30° C. The process of the present invention can be conducted at temperatures below −10° C. but at lower temperatures the danger of freezing of the aqueous mixture becomes greater and reaction times become longer. The use of antifreeze compounds may permit operation of the present process at temperatures lower than −10° C. without freezing. The process of the present invention can also be carried out at temperature above 30° C. but at higher temperatures the risk of side reactions, azo decomposition and lower product yields becomes a serious consideration. Thus, the process of the present invention may be conducted at a temperature that is above the freezing point of the reaction mixture and below the decomposition temperature of the azodinitrile compounds. For example, the azo compound prepared in Example 31 is very sensitive and appreciable decomposition begins to take place above 30° C. The azo compound of Example 22 however is not very sensitive and no appreciable decomposition occurs at 40° C. but there is a tendency for undesirable by-products to be produced at above 30° C.

The time required to complete the reaction of the present invention is dependent on temperature. At the preferred temperature range of 5°–15° C., the reaction takes from about 10 minutes to 30 minutes. At a temperature of −5° C., the reaction will take well over 1 hour. At 30° C., the reaction can be complete in 5 minutes. The time required for the reaction for a specific product at a specific temperature and batch size can readily be determined.

The yields attained by the process of the present invention are substantially greater than the yields attained by the process described in Fuch's U.S. Pat. No. 3,783,148 involving methanol. For example, 2,2'-azobis(2,4-dimethylpentanonitrile) can be prepared in over 95% yield using the process of the present invention as compared to only 80% yield according to U.S. Pat. No. 3,783,148.

Generally, the pressure in the process of the present invention is atmospheric.

The invention is further illustrated by the examples that follow, wherein all percentages are by weight unless otherwise indicated.

EXAMPLE 1A

A mixture of 121 g. 15.9% sodium hypochlorite solution, 93 g. water and 0.6 g. Arquad 16–50% a 50% hexadecyltrimethyl ammonium chloride commodity, was cooled at 5° C. and stirred and 30 g. of 2-amino-2,4-dimethylpentanenitrile of 87% purity was added in 15 min. The equivalent ratio of NaOCl-to-aminonitrile was 1.25, the concentration of NaOCl into which the aminonitrile was introduced was 9% and the amount of surfactant used (100% basis) was 1% of the weight of the aminonitrile. The reaction mixture was stirred 15 min. at 5°–10° C. and then cooled at 5° C. as 70 ml. of a 19% solution of sodium bisulfite, followed by 10 ml. concentrated hydrochloric acid was added. The bisulfite and acid effectively destroyed residual NaOCl and chloramine compounds present and broke the product emulsion during the 15 min. additional stirring time allowed. There was obtained a 7.9% solids slurry which, after filtering, washing and drying gave 24.8 g. of 2,2'-azobis(2,4-dimethylpentanenitrile) which was assayed by a nitrogen evolution eudiometric technique as 99% pure. The yield was 95.5%.

The eudiometric technique for determining purity of the azodinitriles of this invention is readily available in E. I. du Pont de Nemours and Company, Standard Method No. V 38.029(B) (Industrial Chemicals Dept.) published 1/17/69, entitled *Vazo Vinyl Polymerization Catalyst-Determination of Assay-Pyrolytic, Eudiometric Method*.

EXAMPLE 1B

In order that a comparison can be made of the process of the present invention illustrated in Example 1A, 2,2'-azobis(2,4-dimethylpentanenitrile) was prepared according to the teaching of Fuchs, U.S. Pat. No. 3,783,148, using his preferred conditions:

To a rapidly stirred 634 ml. of methanol cooled at −5° C. was added simultaneously 60 g. 2-amino-2,4-dimethylpentanenitrile (87% purity) and 310.2 g. 15.9% sodium hypochlorite solution at a rate such that the addition of reactants was completed at the same time in 1 hr. The equivalent ratio of NaOCl-to-aminonitrile was 1.6. After 10 min. stirring at −5° C., the mixture was allowed to warm to 10° C. and stirred 10 min. at this temperature. To the mixture was now added 425 ml. water to effect precipitation of the product. A 2.9% solids slurry was obtained. The solids was filtered, washed thoroughly and dried to give 41.1 g. product, an 80.0% yield.

Therefore, a higher yield of product is obtained (95.5% vs. 80.0%) using the process of the present invention.

EXAMPLES 2–10

Following the procedure described in Example 1A but substituting equivalent amounts of the aminonitrile starting materials shown for the aminonitrile of Example 1A, the corresponding azonitrile products are obtained in superior yields:

| Example | Aminonitrile Starting Material | Azonitrile Product |
|---|---|---|
| 2 | 2-Amino-2-methylbutyronitrile | 2,2'-Azobis(2-methylbutyronitrile) |
| 3 | 2-Amino-2-methyldecanenitrile | 2,2'-Azobis(2-methyldecanonitrile) |
| 4 | 1-Aminocyclododecanecarbonitrile | 1,1'-Azobis(cyclododecanecarbonitrile) |
| 5 | 2-Amino-2,4,4-trimethylpentanenitrile | 2,2'-Azobis(2,4,4-trimethylpentanonitrile) |
| 6 | 2-Amino-2-isobutyl-4-methylpentanenitrile | 2,2'-Azobis(2-isobutyl-4-methylpentanonitrile) |
| 7 | 2-Amino-4-carboxy-2-methylbutyronitrile | 2,2'-Azobis(4-carboxy-2-methylbutyronitrile) |
| 8 | 2-Amino-4-butoxy-2,4-dimethylpentanenitrile | 2,2'-Azobis(4-butoxy-2,4-dimethylpentanonitrile) |
| 9 | 2-Amino-2-cyclopropylpropanenitrile | 2,2'-Azobis(2-cyclopropylpropionitrile) |
| 10 | 2-Amino-2-methyl-5-hydroxypentanenitrile | 2,2'-Azobis(2-methyl-5-hydroxypentanonitrile) |

EXAMPLES 11–15

Following the procedure of Example 1A the azonitrile, 2,2'-azobis(2,4-dimethylpentanenitrile) is prepared in 98-99% purity by substituting the following equivalent ratios of sodium hypochlorite-to-aminonitrile. The amount of water used is adjusted to give a 9% NaOCl solution in all examples.

| Example | Equivalent Ratio NaOCl/Aminonitrile | Approx. Yield of Azonitrile (%) |
|---|---|---|
| 11 | 1.2:1.0 | 88 –92.2% |
| 12 | 1.4:1.0 | 92 –96% |
| 13 | 1.6:1.0 | 92 –95.5% |
| 14 | 1.8:1.0 | 90.0–91.5% |
| 15 | 2.0:1.0 | 87.0–90.0% |

EXAMPLES 16–21

The azonitrile, 2,2'-azobis(2,4-dimethylpentanenitrile), is prepared in high purity and acceptable yields according to the procedure of Example 1A, substituting the following cationic surfactants for Arquad 16-50 in the amounts denoted.

| Example | Cationic Surfactant | Weight % of Surfactant Based on the Aminonitrile |
|---|---|---|
| 16 | Cetyl trimethyl ammonium bromide (Du Pont Retarder LAN) | 0.5 |
| 17 | Quaternized polyoxyethylene cocoamine (Ethoquad C/25) | 5.0 |
| 18 | Lauryl dimethyl amine oxide (Conco XA-L) | 6.7 |
| 19 | Tallow Trimethyl ammonium chloride (Arquad T-50) | 8.0 |
| 20 | Oleic hydroxyethyl imidazoline (Alkazine O) | 10.0 |
| 21 | 50/50 Wt. mixture surfactants from Examples 16 and 17 | 5.0 |

EXAMPLE 22

To 355 ml. water containing 5 g. Merpol HCS (HLB number of 15.5), a 60% polyoxyethylene lauryl ether commodity was added simultaneously over a period of 30 min. 60 g. of 1-amino-cyclohexanecarbonitrile of 83% purity and 355 g. 15.1% sodium hypochlorite solution with stirring. A reaction mixture temperature of 20°–25° C. was maintained. The addition rates were controlled such that the aminonitrile and hypochlorite additions were completed at the same time. The equivalent ratio of NaOCl-to-aminonitrile was 1.8 and the amount of nonionic surfactant used (100% basis) was 5% of the aminonitrile weight. The reaction mixture was stirred for 5 min. at 20°–25° C., then treated with 140 ml. 19% NaHSO$_3$ and 25 ml. conc. HCl as described in Example 1A. There was obtained 40.1 g. 1,1'-azobis(cyclohexanecarbonitrile) of 98.5% purity, an 85% yield.

EXAMPLES 23–29

The azonitrile, 1,1'-azobis(cyclohexanecarbonitrile), is prepared in high purity and acceptable yields according to the procedure of Example 22, substituting the following nonionic surfactants for Merpol HCS.

| Example | Nonionic Surfactant |
|---|---|
| 23 | Polyoxyethylene (20) sorbitan monolaurate (Tween 60) |
| 24 | Polyoxyethylene glycol (400) monostearate (Emcol H-35A) |
| 25 | Octylphenoxy(ethyleneoxy)ethanol (Igepal CO-630) |
| 26 | Condensate ethylene oxide-propylene oxide-propylene glycol (Pluronic L-64) |
| 27 | Condensate propylene oxide-ethylene oxide-ethylene glycol (Pluronic 17R8) |
| 28 | Ethoxylated coco amine (Varonic K215) |
| 29 | Mixture of surfactants from Examples 23 and 24 (50/50 wt.) |

EXAMPLE 30

Ninety grams of 2-amino-2,4-dimethyl-4-methoxypentanenitrile of 88% purity was added in a time of 25 min. to a stirred solution of 242 g. of 15.6% sodium hypochlorite, 444 g. of water and 7.2 g. of GAFAC LO-529 organic phosphate salt that was cooled at −5° C. The equivalent ratio of NaOCl-to-aminonitrile was 1.5, the NaOCl concentration was 7% and the amount of anionic surfactant was 6.3% of the aminonitrile weight. The reaction mixture was stirred 2 hours. at −5° C., then treated with 210 ml. of 19% NaHSO$_3$ solution and 30 ml. of conc. HCl as described in Example 1A. There was obtained 54 g. 2,2'-azobis(2,4-dimethyl-4-methoxypentanenitrile) of 98% purity with a 70% yield.

EXAMPLE 31

An equimolar mixture of 28.7 g. of 77% purity 2-amino-2-methylbutyronitrile and 31.4 g. of 90.5% purity 2-amino-2-methylhexamentrile was added in 15 min. to a stirred solution of 620 g. of 7.5% sodium hypochlorite solution containing 1.2 g. of octadecyltrimethyl ammonium bromide cooled at 10° C. The equivalent ratio of NaOCl-to-aminonitrile was 1.4 and the amount of cationic surfactant was 2% of the aminonitrile weight. The mixture was stirred for 30 min. at 10° C. then treated with 140 ml. of 19% NaHSO$_3$ and 20 ml. conc. HCl as described in Example 1A. A liquid upper layer was separated and washed with a 5% NaHCO$_3$ solution and then with water twice and dried over anhydrous calcium sulfate. There was obtained 44.6 g. clear, pale yellow liquid composed of three azonitriles, two symmetrical compounds, 2,2'-azobis(2-methylbutyronitrile) and 2,2'-azobis(2-methylhexanonitrile), and an unsymmetrical compound, 2-[(1-cyano-1-methylpropyl)azo]-2-methylhexanentrile.

The yield of product was 90.0%. The product was assayed as 90.0% pure by a nitrogen evolution eudiometric technique.

EXAMPLES 32-33

By substituting equivalent amounts of the aminonitrile starting materials shown below for the aminonitriles in Example 31, the corresponding liquid azonitrile products are obtained in about 90% yield.

32.

STARTING MATERIALS

2-Amino-2-methylbutyronitrile and
2-Amino-2-methylheptanenitrile.

AZONITRILES 2,2'-Azobis(2-methylbutyronitrile),
2,2'-Azobis(2-methylheptanenitrile) and
2-[(1-Cyano-1-methylpropyl)azo]-2-methylheptanenitrile.

33.

STARTING MATERIALS

2-Amino-2-methylbutyronitrile and
2-Amino-2-ethylhexanenitrile.

AZONITRILES 2,2'-Azobis(2-methylbutyronitrile),
2,2'-Azobis(2-ethylhexanenitrile) and
2-[(1-Cyano-1-methylpropyl)azo]-2-ethylhexanenitrile.

EXAMPLE 34

Three hundred fifty grams of 15.2% solution of sodium hypochlorite, 240 g. water, 0.9 g. of a 20% solution of hexadecyltrimethyl ammonium bromide and 5 drops of GE Antifoam 93 were mixed, cooled to −3° C. and stirred as 60 g. of 2-amino-2-methylpropanenitrile of 80% purity was added in 20 minutes. The temperature was maintained between −3° C. and +2° C. during the addition and for 30 minutes longer, then allowed to rise to +5° C. for an additional 30 minutes period. The equivalent ratio of NaOCl-to-aminonitrile was 1.25, the initial concentration of NaOCl into which the amino compound was added was 9% and the amount of surfactant used (100% basis) was 0.3% of the aminonitrile weight. During the reaction period it was noted that the product formed was a suspension. No emulsion breaking or precipitation agent were added. The product filtered rapidly and weighed 45.2 g., a 96.5% yield, after washing and drying and was determined as being 2,2'-azobis(isobutyronitrile).

EXAMPLE 35

Sixty pounds of ammonia-free 2-amino-2-methylpropanenitrile of 75.1% purity was added in 20 minutes to a rapidly stirred mixture of 396 lb. 12.6% sodium hypochlorite solution, 158 lb. water, 0.9 lg. of a 20 % solution of hexadecyltrimethyl ammonium bromide and 0.1 lg. Antifoam 93 (Dow-Corning) cooled at 0° C. The mole ratio of NaOCl/aminonitrile = 1.25.

The percent of surfactant may be expressed as 0.3% of the aminonitrile weight.

The percent NaOCl in the mixture to which the aminonitrile was added was 9.0.

After the addition was completed, the reaction mixture was stirred at 0° C. for 30 minutes and at 10° C. for 1 hour.

Filtration gave a white product which, after washing and drying, amounted to 43.3 lb., a 98.4% yield of 2,2′-azobis(2-methylpropanenitrile).

The azodinitrile compounds of the present invention are useful as initiators in free radical polymerization reactions.

While certain representative embodiments and details have been shown for the purpose of illustrating the invention, it will be apparent to those skilled in this art that various changes and modifications may be made therein without departing from the spirit or scope of the invention.

What is claimed is:

1. The process for the preparation of azodinitriles comprising reacting an alpha-aminonitrile selected from the group consisting of

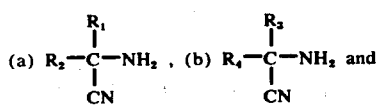

mixtures of (a) and (b) wherein $R_1$, $R_2$, $R_3$ and $R_4$ are selected from the group consisting of (1) acylic aliphatic hydrocarbon radicals of 1 to 9 carbon atoms, (2) carbon acylic aliphatic radicals of 1 to 8 carbon atoms substituted with carboxyl, hydroxyl or —OR wherein R is selected from an acyclic aliphatic hydrocarbon radical of 1 to 4 carbon atoms, (3) cyclic aliphatic hydrocarbon radicals of 3 to 6 carbon atoms and (4) cyclic aliphatic hydrocarbon radicals of 3 to 11 carbon atoms formed by combining $R_1$ and $R_2$ or $R_3$ and $R_4$, with 5 to 15% by weight based on the reaction mixture of a metal hypochlorite, $M(OCl)_x$ where M is selected from sodium, potassium or calcium and $x$ is the valence of M, in an aqueous medium in the presence of 0.25 to 10% by weight based on the weight of aminonitrile of a surface active compound or mixtures thereof having an HLB of 8 to 35 at a temperature of −10° C to 30° C said metal hypochlorite and alpha-aminonitrile being present in an equivalent ratio of from 1:1 to 2:1 of hypochlorite to aminonitrile and recovering from the reaction mixture an aliphatic azodinitrile compound of the formula

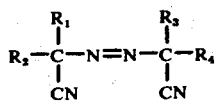

wherein $R_1$, $R_2$, $R_3$ and $R_4$ are as defined and $R_1$ and $R_2$ may be the same as $R_3$ and $R_4$.

2. The process of claim 1 wherein the equivalent ratio of hypochlorite to aminonitrile is from 1.2:1 to 1.8:1.

3. The process of claim 1 wherein the metal, M, is sodium.

4. The process of claim 1 wherein the surface active compound is 1.0 to 4.0% by weight of the aminonitrile.

5. The process of claim 1 wherein the surface active compound is selected from (1) cationic, (2) anionic, (3) nonionic, (4) amphoteric and (5) mixtures of at least two surfactants selected from cationic, anionic, non-ionic, and amphoteric surfactants.

6. The process of claim 1 wherein the surface active compound is cationic.

7. The process of claim 1 wherein the temperature is from 5° C to 15° C.

8. The process of claim 1 wherein the alpha-aminonitrile is 2-amino-2,4-dimethylpentanenitrile and the azodinitrile is 2,2′-azobis-(2,4-dimethylpentanenitrile).

9. The process of claim 1 wherein the alpha-aminonitrile is 1-amino-cyclohexanecarbonitrile and the azodinitrile is 1,1′-azobis(cyclohexanecarbonitrile).

10. The process of claim 1 wherein the alpha-aminonitrile is 2-amino-2,4-dimethyl-4-methoxypentanenitrile and the azodinitrile is 2,2′-azobis(2,4-dimethyl-4-methoxypentanenitrile).

11. The process of claim 1 wherein the alpha-aminonitrile is a mixture of 2-amino-2-methylbutyronitrile and 2-amino-2-methylhexanenitrile and the azodinitrile is 2-[(1-cyano-1-methylpropyl)azo]-2-methylthexanenitrile.

12. The process of claim 6 wherein the cationic surface active compound is a tetraalkyl ammonium halide.

13. The process of claim 6 wherein the cationic surface active compound is an alkyl trimethyl ammonium chloride or bromide.

14. The process of claim 6 wherein the cationic surface active compound is hexadecyl trimethyl ammonium chloride.

15. The process of claim 1 wherein the surface active compound is nonionic.

16. The process of claim 15 wherein the nonionic surface active compound is selected from the group consisting of a condensate of ethylene oxide or propylene oxide with a propylene or ethylene glycol, polyoxyalkylene fatty acid esters, polyoxyalkylene alkyl ethers, polyoxyalkylene fatty alcohol ethers and polyoxyethylene sorbitan fatty acid esters.

17. The process of claim 15 wherein the nonionic surface active compound is a polyoxyethylene lauryl ether.

18. The process of claim 1 wherein the HLB range is from 8 to 30.

19. The process of claim 1 wherein the HLB range is from 12 to 15.

20. The process of claim 1 wherein the alpha-aminonitrile is 2-amino-2-methylpropanenitrile and the azodinitrile is 2,2′-azobis(isobutyronitrile).

* * * * *

UNITED STATES PATENT OFFICE
CERTIFICATE OF CORRECTION

PATENT NO. : 4,028,345
DATED : JUNE 7, 1977
INVENTOR(S) : EARL PHILLIP MOORE, JR.

It is certified that error appears in the above-identified patent and that said Letters Patent are hereby corrected as shown below:

In the Abstract, 5 lines from the bottom, after "ratio of" add -- from --.

Column 1, line 47, "keton" should be -- ketone --.

Column 2, line 26, "would" should be -- could --.

Column 3, line 25, "produce" should be -- product --.

Column 4, line 53, "described" should be -- desired --.

Column 5, line 45, "methoxypentanonitrile" should be -- methoxypentanenitrile --.

Column 6, line 7, "or" should be -- of --.

Column 6, lines 18-19, "handling" should be -- handle --.

Column 6, line 20, "not" should be -- no --.

Column 7, line 22, "preferred" should be -- prepared --.

Column 7, line 44, "Americal" should be -- American --.

Column 10, line 25, "temperature" should be -- temperatures --.

Column 13, line 53, "methylhexamentrile" should be -- methylhexanenitrile --.

Column 14, line 47, "minutes" should be -- minute --.

UNITED STATES PATENT OFFICE
CERTIFICATE OF CORRECTION

PATENT NO. : 4,028,345
DATED : JUNE 7, 1977
INVENTOR(S) : EARL PHILLIP MOORE, JR.

It is certified that error appears in the above-identified patent and that said Letters Patent are hereby corrected as shown below:

Column 14, line 63, "0.9 lg." should be -- 0.9 lb. --.

Column 14, line 65, "0.1 lg." should be -- 0.1 lb. --.

Column 15, line 30, "acylic" should be -- acyclic --.

Column 15, line 31, "9" should be -- 8 --.

Column 15, line 32, "carbon acylic" should be -- acyclic --.

Column 15, line 58, after "defined" add -- above --.

Column 16, line 31, "methylthexanenitrile" should be -- methylhexanenitrile --.

UNITED STATES PATENT OFFICE
CERTIFICATE OF CORRECTION

PATENT NO. : 4,028,345
DATED : JUNE 7, 1977
INVENTOR(S) : EARL PHILLIP MOORE, JR.

It is certified that error appears in the above-identified patent and that said Letters Patent are hereby corrected as shown below:

Column 16, line 45, after "alkyl" add -- aryl --.

Column 16, line 55, "15" should be -- 35 --.

Signed and Sealed this

Twenty-ninth Day of November 1977

[SEAL]

Attest:

RUTH C. MASON
Attesting Officer

LUTRELLE F. PARKER
Acting Commissioner of Patents and Trademarks